(12) United States Patent
Wells et al.

(10) Patent No.: US 12,257,240 B2
(45) Date of Patent: Mar. 25, 2025

(54) COMBINATION OF BERBERINE AND DERIVATIVES THEREOF, AND VITAMIN B12

(71) Applicant: NANJING NUTRABUILDING BIO-TECH CO., LTD., Nanjing (CN)

(72) Inventors: Shawn Wells, Lewisville, TX (US); Ronghua Yi, Nanjing (CN); Mingru Wang, Nanjing (CN); Kylin Liao, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 0 days.

(21) Appl. No.: 17/893,634

(22) Filed: Aug. 23, 2022

(65) Prior Publication Data
US 2023/0067847 A1 Mar. 2, 2023

(51) Int. Cl.
*A61K 31/4375* (2006.01)
*A61K 31/714* (2006.01)
*A61P 7/00* (2006.01)

(52) U.S. Cl.
CPC ........ *A61K 31/4375* (2013.01); *A61K 31/714* (2013.01); *A61P 7/00* (2018.01)

(58) Field of Classification Search
CPC .............. A61K 31/4375; A61K 31/714; A61K 2300/00; A61P 7/00; A61P 3/04; A61P 3/10; A23L 33/10; A23L 33/15; A23V 2002/00; A23V 2200/328; A23V 2200/332; A23V 2250/706
See application file for complete search history.

(56) References Cited

FOREIGN PATENT DOCUMENTS

| AU | 2005284528 A1 | * | 5/2007 | ......... A61K 31/4375 |
|---|---|---|---|---|
| CN | 101584709 A | * | 11/2009 | |
| EP | 3456328 A1 | | 3/2019 | |
| JP | 2011213667 A | * | 10/2011 | |
| WO | 2016107603 A1 | | 7/2016 | |

OTHER PUBLICATIONS

Degnan, Patrick H., Taga, Michiko&E., & Goodman, Andrew L. Vitamin B 12 as a Modulator of Gut Microbial Ecology. Cell Metabolism, 20(5), 769-778. https://doi.org/10.1016/j.cmet.2014.10.002 (Year: 2014).*
Di Pierro et al. Pilot study on the additive effects of berberine and oral type 2 diabetes agents for patients with suboptimal glycemic control. Diabetes, Metabolic Syndrome and Obesity: Targets and Therapy, 5(vol. 5, 2012), 213-217. https://doi.org/10.2147/DMSO.S33718 (Year: 2012).*
Byakodi, R. 15 Signs and Symptoms of Vitamin B12 Deficiency. Best for Nutrition. https://bestfornutrition.com/15-signs-symptoms-of-vitamin-b12-deficiency/#1-15-signs-of-vitamin-b12-deficiency (Year: 2020).*
Cheng et al. 8,8-Dimethyldihydroberberine with improved bioavailability and oral efficacy on obese and diabetic mouse models. Bioorganic & Medicinal Chemistry, 18(16), 5915-5924. https://doi.org/10.1016/j.bmc.2010.06.085 (Year: 2010).*
Pang, B., Zhao, L.-H., Zhou, Q., Zhao, T.-Y., Wang, H., Gu, C.-J., & Tong, X.-L.. Application of Berberine on Treating Type 2 Diabetes Mellitus. International Journal of Endocrinology, 2015, 1-12. https://doi.org/10.1155/2015/905749 (Year: 2015).*
Reagan-Shaw, S., Nihal, M., & Ahmad, N. Dose translation from animal to human studies revisited. The FASEB Journal, 22(3), 659-661. https://doi.org/10.1096/fj.07-9574lsf (Year: 2007).*
Machine Translation of CN101584709A (Year: 2009).*
Kibirige et al. Vitamin B12 deficiency among patients with diabetes mellitus: is routine screening and supplementation justified? Journal of Diabetes and Metabolic Disorders, 12, 17. https://doi.org/10.1186/2251-6581-12-17 (Year: 2013).*
Ahmed, S., & Rohman, S. Study of serum Vitamin B12 and its correlation with Lipid profilein Type 2 Diabetes Mellitus. Indian J Basic Appl Med Res, 5(4), 92-103. (Year: 2016).*
Bhise, S. B., Kadam, Y. D., & Ismaeel, G. L. Effect of Vitamin B12 Supplement in Metformin Treated Diabetic Patients and it's Correlation to Peripheral Neuropathy. International Journal of Pharma Research and Health Sciences, 6(2). https://doi.org/10.21276/ijprhs.2018.2018.02.09 (Year: 2018).*
Langan, R. C., & Goodbred, A. J. Vitamin B12 Deficiency: Recognition and Management. Am Fam Physician, 96(6), 384-398. https://doi.org/10.1097/00129300-200206000-00001 (Year: 2017).*
Nair, A. B., & Jacob, S. A Simple Practice Guide for Dose Conversion between Animals and Human. Journal of Basic and Clinical Pharmacy, 7(2), 27. https://doi.org/10.4103/0976-0105.177703 (Year: 2016).*
Kibirige, D., & Mwebaze, R. Vitamin B12 deficiency among patients with diabetes mellitus: is routine screening and supplementation justified? Journal of Diabetes and Metabolic Disorders, 12, 17. https://doi.org/10.1186/2251-6581-12-17 (Year: 2013).*
Turner et al. Berberine and Its More Biologically Available Derivative, Dihydroberberine, Inhibit Mitochondrial Respiratory Complex I: A Mechanism for the Action of Berberine to Activate AMP-Activated Protein Kinase and Improve Insulin Action. Diabetes, 57(5), 1414-1418. (Year: 2008).*

* cited by examiner

*Primary Examiner* — Yih-Horng Shiao
*Assistant Examiner* — Hoi Yan Lee
(74) *Attorney, Agent, or Firm* — ANOVA LAW GROUP, PLLC

(57) ABSTRACT

Among others, the present invention provides methods and compositions for controlling blood glucose or weight, including a combination of (i) a therapeutically effective amount of berberine (BBR), or a pharmaceutically acceptable salt, acid, ester, analog or derivative thereof, including dihydroberberine (DHB); and (ii) vitamin B12. The combination effectively ameliorates BBR or DHB side effects, including VB12 reduction, gastrointestinal discomfort, and slowed bowel movements, by promoting transcobalamin II receptors synthesis, decreasing homocysteine levels and maintaining intestinal balance, including short chain fatty acids content, gut microbiota diversity and richness.

10 Claims, 6 Drawing Sheets

COMBINATION OF BERBERINE AND DERIVATIVES THEREOF, AND VITAMIN B12

CROSS REFERENCE TO RELATED APPLICATION

This application claims the benefit of a PCT International Application Number PCT/CN2021/114828, filed on Aug. 26, 2021, the content of which is hereby incorporated by reference in its entirety for all purposes.

FIELD OF THE INVENTION

This invention generally relates to the field of compositions and methods for controlling blood glucose and weight (e.g., treatment of diabetes), and more specifically relates to a combination, composition or kit comprising (i) berberine (BBR), or a pharmaceutically acceptable salt, acid, ester, analog or derivative thereof (e.g., dihydroberberine (DHB)), and (ii) vitamin B12 (VB12), for controlling blood glucose and weight, while ameliorating BBR/DHB-related side effects, such as VB12 reduction, gastrointestinal discomfort, and slowed bowel movements.

BACKGROUND OF THE INVENTION

Recent studies have shown that, traditional Chinese medicine, called berberine (BBR, a natural plant alkaloid extracted from *Berberis aristata* and *Coptis chinensis* (Huanglian)) or dihydroberberine (DHB, a hydrogenated derivative of BBR) may have potentials to be used for controlling arrhythmia, losing weight, lowering blood lipid, lowering blood pressure, reducing blood sugar and treating T2DM. See, Dong, H., et al., *Berberine in the treatment of type 2 diabetes mellitus: a systemic review and meta-analysis*. Evid Based Complement Alternat Med, 2012. 2012: p. 591654.12; and Dong, H., et al., The effects of berberine on blood lipids: a systemic review and meta-analysis of randomized controlled trials. Planta Med, 2013. 79(6): p. 437-46. In particular, DHB is one of BBR metabolites, a product of reduction via nitroreductases within the gut microbiota. See, e.g., Mohammad, M., et al., *Inhibition of pancreatic lipase by berberine and dihydroberberine: an investigation by docking simulation and experimental validation*. Medicinal Chemistry Research, 2013. 22(5): p. 2273-2278; and Feng, R., et al. Transforming berberine into its intestine-absorbable form by the gut microbiota. Scientific reports, 2015. 5, 12155 DOI:

However, like metformin, BBR/DHB has a disruption of the Ca-dependent absorption at the terminal ileum and at TCII receptors synthesis. The levels of VB12-IF and VB12-TCII can be impacted by BBR/DHB because of a Ca-dependent ileal membrane antagonism, such that VB12 level may be affected. In addition, BBR/DHB exerts an alteration in intestinal balance such as short chain fatty acids content, gut microbiota diversity and richness. That is to say, there are some side effects associated with BBR/DHB. Thus, there is an urgent need to find an effective strategy to ameliorate undesired side effects, including VB12 reduction, gastrointestinal discomfort, and slowed bowel movements.

SUMMARY OF THE INVENTION

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

The present invention generally relates to a combination or use of (i) berberine (BBR), or a pharmaceutically acceptable salt, acid, ester, analog or derivative thereof (particularly dihydroberberine (DHB)); and (ii) vitamin B12 (VB12), for controlling blood glucose or weight or treating diabetes (e.g., type 2 diabetes mellitus (T2DM)), while ameliorating BBR/DHB-related side effects. In particular, inventors of the present application speculated and found that BBR/DHB may have similar pathways as metformin, and thus also affect the absorption of VB 12. It was also found that the BBR/DHB-related side effects (e.g., VB12 deficiency) could be successfully mitigated by combining with VB12 supplements (e.g., man-made forms of VB12 such as cyanocobalamin). According to the present invention, the combination of BBR/DHB and vitamin B12 can particularly ameliorate vitamin B12 reduction by promoting transcobalamin II receptors synthesis, decreasing homocysteine levels and maintaining intestinal balance, such as short chain fatty acids content, gut microbiota diversity and richness.

One aspect of the present invention provides a method for controlling blood glucose or weight or treating diabetes (e.g., type 2 diabetes mellitus (T2DM)), including administrating to the mammal in need thereof a combination including: (i) a therapeutically effective amount of berberine (BBR), or a pharmaceutically acceptable salt, acid, ester, analog or derivative thereof; and (ii) vitamin B12 (VB12). In some embodiments, the combination effectively ameliorates BBR or BBR derivative-related side effects.

In some embodiments, the combination includes (i) a hydrogenated derivative of BBR being dihydroberberine (DHB); and (ii) VB12.

In some embodiments, the side effects include gastrointestinal discomfort, slowed bowel movements, or VB12 reduction. Particularly, the side effects may include VB12 reduction.

In some embodiments, the combination is prepared as a food, a drink, a supplement, or a pharmaceutical formulation.

In some embodiments, the combination is in the form of suppository, tablet, pill, granule, powder, film, (micro)capsule, aerosol, tonic, liquid suspension, injection or syrup.

In some embodiments, the combination is administrated by one or multiple routes selected from oral, intravenous injectable, intramuscular injectable, intraperitoneal, and sublingual administrations.

In some embodiments, the combination can preserve Ca-dependent membrane function at the terminal ileum, promote TCII receptors synthesis, and/or mitigate or increase VB12-IF levels and decrease homocysteine levels of mammals daily.

In some embodiments, the combination can maintain intestinal balance of mammals daily, such as short chain fatty acid (SCFAs) contents of mammals with normal limit, and gut microbiota diversity and richness of mammals.

In some embodiments, the mammal is a human or animal.

In some embodiments, the ratio of BBR/DHB and VB12 is 2:98 to 98:2. The ratio is preferably 6:94 to 94:6, more preferably 16:84 to 84:16, most preferably 32:68 to 68:32.

In some embodiments, the combination of BBR/DHB and VB12 is configured for administration at a dosage ranging from 20 mg to 600 mg per serving. Preferably, it is administered at a dosage ranging from 40 mg to 300 mg per serving, and the administration may last for at least two weeks.

In some embodiments, the combination of BBR/DHB and VB12 is administrated once a day, twice a day, or three times a day.

In some embodiments, BBR/DHB and VB12 are administrated simultaneously or sequentially.

Another aspect of the present invention provides a composition including a combination of (i) berberine (BBR), or a pharmaceutically acceptable salt, acid, ester, analog or derivative thereof, and (ii) vitamin B12 (VB12), for controlling blood glucose or weight and ameliorating BBR or BBR derivative-related side effects. Specifically, the composition may include (i) a hydrogenated derivative of BBR being dihydroberberine (DHB); and (ii) VB12.

In some embodiments, the composition is for treating diabetes.

In some embodiments, the side effects include gastrointestinal discomfort, slowed bowel movements, or VB12 reduction.

In some embodiments, the composition is a food, a drink, a supplement, or a pharmaceutical formulation.

In some embodiments, the composition is in the form of suppository, tablet, pill, granule, powder, film, (micro)capsule, aerosol, tonic, liquid suspension, injection or syrup.

In some embodiments, the composition is to be administrated into a mammal by oral, intravenous injectable, intramuscular injectable, intraperitoneal, or sublingual route.

In some embodiments, the composition is capable of preserving Ca-dependent membrane function at the terminal ileum, promoting TCII receptors synthesis, and/or mitigating or increasing VB12-IF levels and decreasing homocysteine levels of mammals daily.

In some embodiments, the composition can maintain intestinal balance of mammals daily, e.g., to maintain short chain fatty acid (SCFAs) contents of mammals with normal limit, and gut microbiota diversity and richness of mammals.

In some embodiments, the ratio of BBR/DHB and VB12 is 2:98 to 98:2. The ratio is preferably 6:94 to 94:6, more preferably 16:84 to 84:16, most preferably 32:68 to 68:32.

In some embodiments, the composition is configured for administration at a dosage ranging from 20 mg to 600 mg per serving. Preferably, it is administered at a dosage ranging from 40 mg to 300 mg per serving, and the administration may last for at least two weeks.

In some embodiments, the composition is to be administrated once a day, twice a day, or three times a day.

A further aspect of the present invention is related to use of a composition including berberine (BBR), or a pharmaceutically acceptable salt, acid, ester, analog or derivative thereof, in combination of vitamin B12 (VB12), for controlling blood glucose or weight or treating diabetes. In some embodiments, the composition can be used for ameliorating BBR or BBR derivative-related side effects which include gastrointestinal discomfort, slowed bowel movements, or VB12 reduction.

In some embodiments, the composition includes a hydrogenated derivative of BBR being dihydroberberine (DHB).

Still another aspect of the present invention is related to a kit including (i) a first component including at least one dose of berberine (BBR), or a pharmaceutically acceptable salt, acid, ester, analog or derivative thereof; (ii) a second component including at least one dose of vitamin B12 (VB12), and instructions for a combined administration of VB 12 and berberine (BBR), or a pharmaceutically acceptable salt, acid, ester, analog or derivative thereof, for controlling blood glucose or weight or treating diabetes.

In some embodiments, VB 12 and berberine (BBR), or a pharmaceutically acceptable salt, acid, ester, analog or derivative thereof, are administrated simultaneously or sequentially. For instance, the ratio of BBR/DHB and VB12 may be 2:98 to 98:2. The ratio is preferably 6:94 to 94:6, more preferably 16:84 to 84:16, most preferably 32:68 to 68:32. The combination of BBR/DHB and VB12 may be configured for administration at a dosage ranging from 20 mg to 600 mg per serving. Preferably, it is administered at a dosage ranging from 40 mg to 300 mg per serving, and the administration may last for at least two weeks. The combination of BBR/DHB and VB12 may be administrated once a day, twice a day, or three times a day.

In some embodiments, the kit includes a hydrogenated derivative of BBR being dihydroberberine (DHB).

In some embodiments, the combined administration ameliorates BBR/DHB-related side effects including gastrointestinal discomfort, slowed bowel movements, or VB12 reduction.

In still a further aspect, the present invention provides a method for preparing a composition for controlling blood glucose or weight or treating diabetes, including preparation of (i) berberine (BBR), or a pharmaceutically acceptable salt, acid, ester, analog or derivative thereof, and (ii) vitamin B12 (VB12).

In some embodiments, the method includes preparation of a hydrogenated derivative of BBR being dihydroberberine (DHB).

In some embodiments, the ratio of BBR/DHB and VB12 is 2:98 to 98:2. The ratio is preferably 6:94 to 94:6, more preferably 16:84 to 84:16, most preferably 32:68 to 68:32.

Still in some embodiments, the composition is prepared in the form of suppository, tablet, pill, granule, powder, film, (micro)capsule, aerosol, tonic, liquid suspension, injection or syrup.

As used herein, the term "or" is meant to include both "and" and "or." In other words, the term "or" may also be replaced with "and/or."

As used herein, the singular forms "a," "an" and "the" are intended to include the plural forms as well, unless the context clearly indicates otherwise.

As used herein, the term "mammal", "animal" or "subject" may be used interchangeably to refer to any animal to which the presently disclosed methods and compositions may be applied or administered. The animal may have an illness or other disease, but the animal does not need to be sick to benefit from the presently disclosed methods and compositions. As such any animal may apply the disclosed combinations, compositions or kits, or be a recipient of the disclosed methods.

Animals can be birds, reptiles and mammals. In certain embodiments, animals can be mammals including non-primates and primates. Typically, an animal as referred to herein includes a human or a domesticated animal. For example, domesticated animals include a dog, cat, or any farm animal including horses, cows, sheep, goats, pigs, or chickens. More typically, an animal could be a human.

As used herein, the term "comprise" or "include" and their conjugations, refer to a situation wherein said terms are used in their non-limiting sense to mean that items following the word are included, but items not specifically mentioned are not excluded. It also encompasses the more limiting verb 'to consist essentially of' and 'to consist of'.

As used herein, the term "administration" refers to the process of delivering a disclosed combination, composition or kit to a subject. The combination, compositions or kits can be administered in a variety of ways, including orally, intragastrically, and parenterally (e.g., intravenous and intraarterial as well as other suitable parenteral routes), and the like.

As used herein, the term "effective amount" refers to the amount required to achieve the effect as taught herein. An effective amount herein includes, but is not limited to, the amount necessary to control blood glucose or weight or treat diabetes in a subject; and/or to ameliorate BBR or BBR derivative-related side effects, such as gastrointestinal discomfort, slowed bowel movements, or VB12 reduction; and/or to preserve Ca-dependent membrane function at the terminal ileum, promote cell surface TCII receptors synthesis, and/or mitigate or increase VB12-IF levels and decrease homocysteine levels of mammals daily; and/or to maintain intestinal balance of mammals daily, maintain SCFAs contents of mammals with normal limit, and gut microbiota diversity and richness of mammals. In accordance with the present disclosure, a suitable single dose size is that which, when administered one or more times over a suitable period of time, achieves the above-described effects.

As used herein, the term "pharmaceutically acceptable" means pharmaceutically, physiologically, alimentarily, or nutritionally acceptable, and refers to those compositions or combinations of agents, materials, or compositions, and/or their dosage forms, which are within the scope of sound medical judgment, suitable for use in contact with the tissues of human beings and animals without excessive toxicity, irritation, allergic response, or other problem or complication, commensurate with a reasonable benefit/risk ratio.

DETAILED DESCRIPTION OF THE INVENTION

Figure 1A:
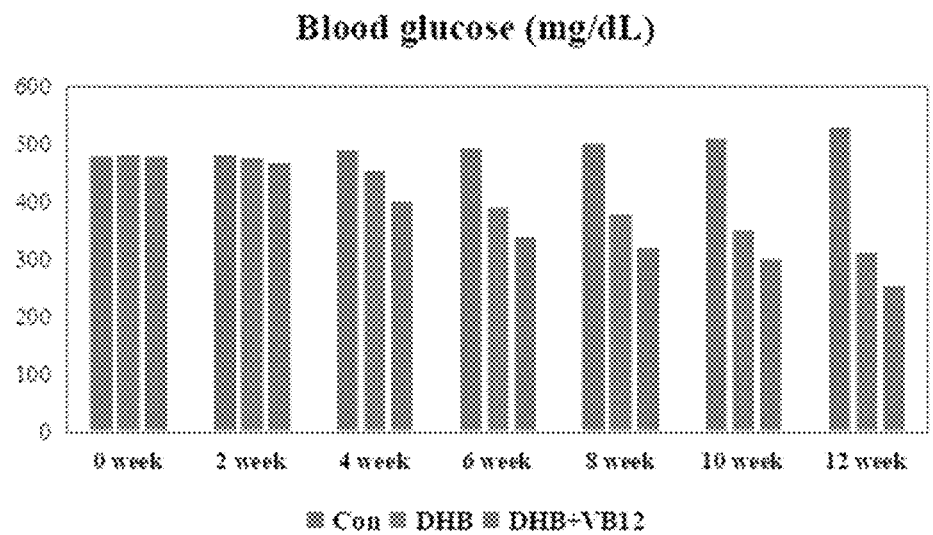
FIG. 1a is a graph of blood glucose levels of three groups of HFD mice (Con; DHB; DHB+VB12) at 0th, 2th, 4th, 6th, 8th, 10th and 12th weeks.
Figure 1B:
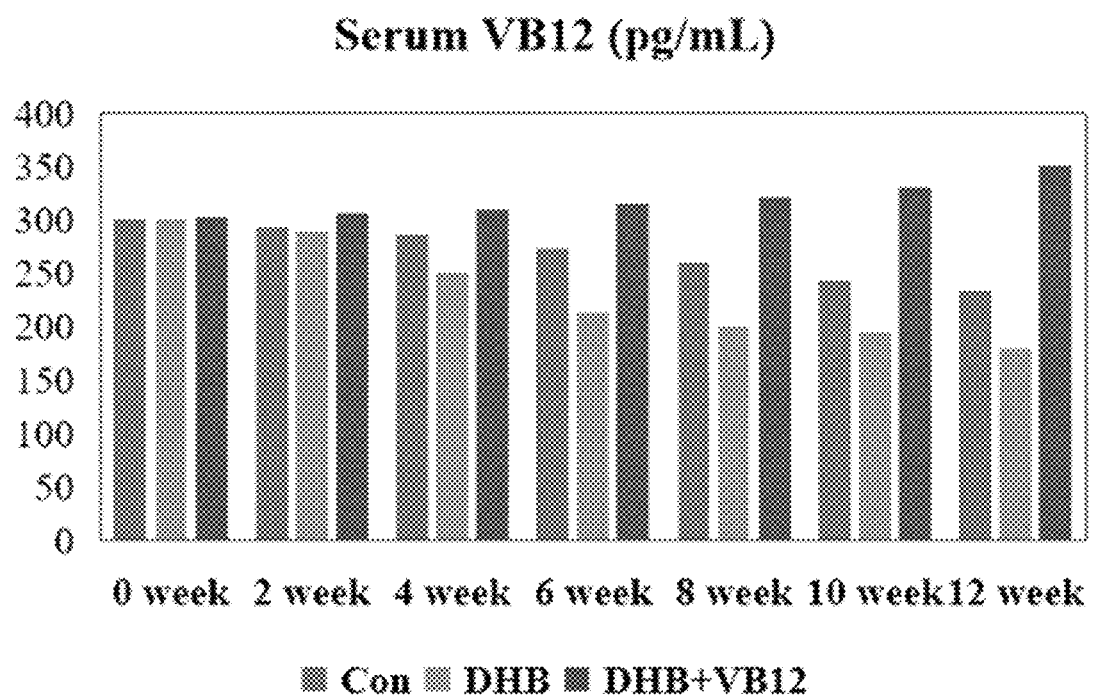
FIG. 1b is a graph of serum VB12 levels of three groups of HFD mice (Con; DHB; DHB+VB12) at 0th, 2th, 4th, 6th, 8th, 10th and 12th weeks.
Figure 1C:
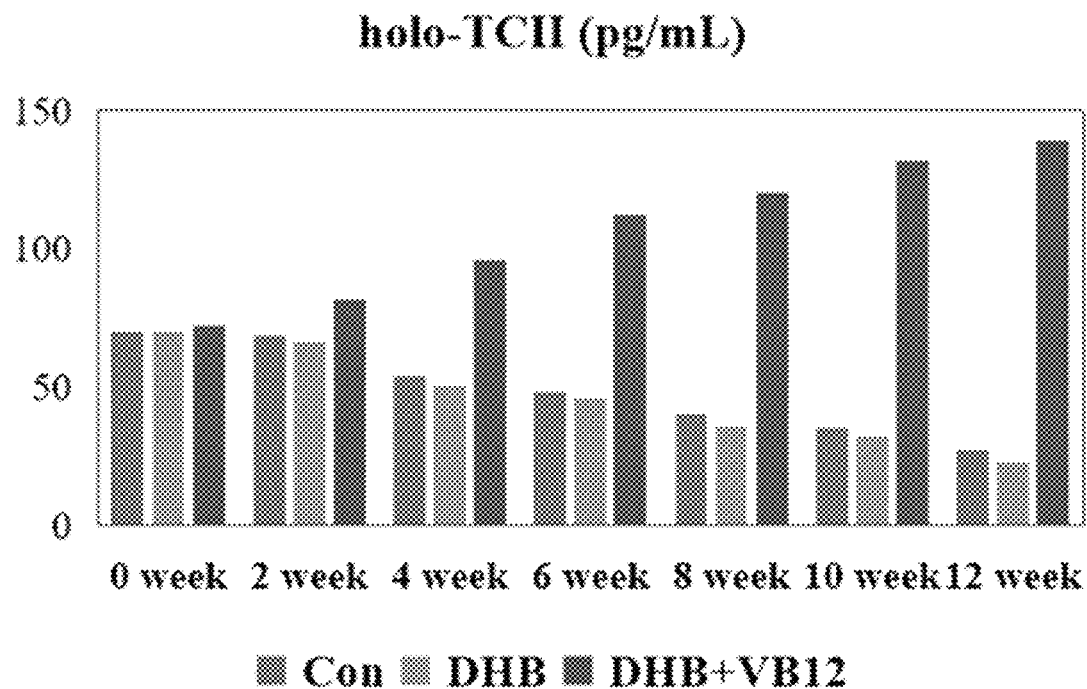
FIG. 1c is a graph of holo-TCII levels of three groups of HFD mice (Con; DHB; DHB+VB12) at 0th, 2th, 4th, 6th, 8th, 10th and 12th weeks.
Figure 1D:
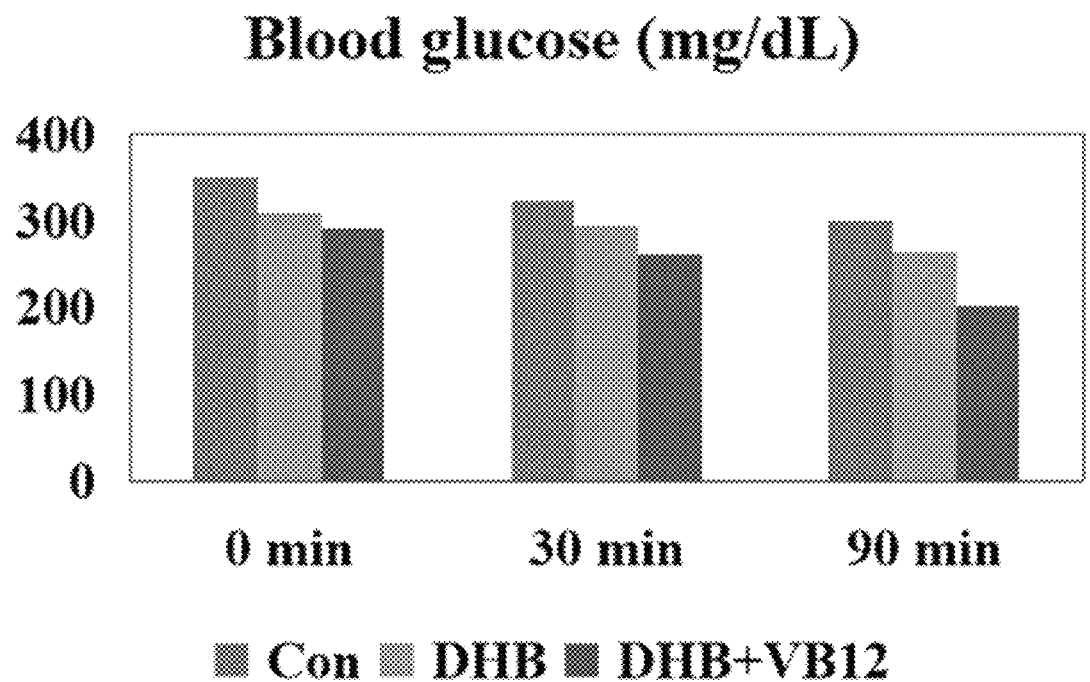
FIG. 1d is a graph of blood glucose levels at 0, 30, and 90 minutes after subcutaneous insulin injection of three groups of HFD mice (Con; DHB; DHB+VB12) without supplement, supplement with DHB, or with DHB+VB 12 for 3 months, respectively.

Reference will now be made in detail to the preferred embodiments of the invention, examples of which are further illustrated. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and other features have not been described in detail as not to unnecessarily obscure aspects of the present invention.

Generally speaking, various embodiments of the present invention provide for combination, combination drug or composition, and combination kit, including (i) berberine (BBR), or a pharmaceutically acceptable salt, acid, ester, analog or derivative thereof (particularly dihydroberberine (DHB)); and (ii) vitamin B12 (VB12)—for controlling blood glucose or weight or treating diabetes (e.g., type 2 diabetes mellitus (T2DM)), while ameliorating BBR/DHB-related side effects.

In particular, inventors of the present application found that BBR/DHB may have similar pathways as metformin, and thus also affect the absorption of VB12.

Conventional metformin was known for its beneficial effects on carbohydrate metabolism (such as use for treatment in patients with type 2 diabetes mellitus (T2DM)), weight loss, and vascular protection. However, metformin has been reported with lots of known and severe side effects. For example, patients on long-term metformin therapy were found to be at risk of anemia and gastrointestinal discomfort, due to a metformin related vitamin B12 (VB12) reduction. VB12 is known as an important water-soluble vitamin for human health, which plays a very fundamental role in DNA synthesis, optimal hemopoiesis and neurological function. The clinical experiment of VB12 malabsorption is predominantly of features of haematological and neurocognitive dysfunction. Moreover, as VB12 can take part in the most important pathway of homocysteine (Hcy) metabolism, VB12 deficiency may result in an increase plasma concentration of Hcy, which is strongly linked to cardiovascular disease, especially in patients with T2DM. In addition, many studies assessing patients with T2DM on metformin have reported the prevalence of VB12 deficiency to range from 5.8% to 33%. While prior publications have reported many reasons of metformin related VB12 reduction, we believe that the following two mechanisms are particularly important reasons.

First, metformin prevents the calcium dependent absorption at the terminal ileum and at transcobalamin II receptors synthesis. Of note, the uptake of VB12-intrinsic factor (IF, a glycoprotein to combine with VB12) complex, that is, the form of VB12 presence in the gastrointestinal tract, at the terminal ileum by the ileal cell surface receptor is calcium (Ca) dependent. Metformin is known to have an effect on Ca-dependent membrane action. In the first place, the hydrophobic tail of metformin, such as methyl group, could extend into the hydrocarbon core of membranes, affecting the Ca-dependent absorption and subsequent influencing the VB12-IF levels. Furthermore, the protonated biguanide group of metformin can provide the positive charge on the membrane surface and then may replace divalent cations such as Ca2+. In addition, the cell surface transcobalamin II (TCII, a receptor to interact with proteolytic release of VB12 and be transported across the human cells) receptors synthesis also depends on Ca. Because of the hydrophobic methyl group and protonated biguanide group of metformin, the synthesis of TCII receptors may be interfered with, resulting in inhibiting binding of the proteolytic release of VB12 and consequential VB12 reduction.

Second, metformin can change ileal morphological structure. The level of VB12-IF complex also depends on ileal morphological structure which relies on the diversity and richness of intestinal microorganisms. Based on our knowledge, gastrointestinal adverse effects were the frequently observed in patients treated with metformin, because metformin, which delays glucose intestinal absorption, slows small bowel motility and stimulates bacterial overgrowth, leading to alter the ileal morphological structure and inhibit VB12 absorption.

Recent studies have shown that, traditional Chinese medicine, called berberine (BBR, a natural plant alkaloid extracted from *Berberis aristata* and Coptis *chinensis* (Huanglian)) or dihydroberberine (DHB, a hydrogenated derivative of BBR) may have potentials to be used for controlling arrhythmia, losing weight, lowering blood lipid, lowering blood pressure, reducing blood sugar and treating T2DM.

According to our study on the similarities between BBR/DHB and metformin, we speculated and found that BBR/DHB, which can control blood glucose, may affect the absorption of VB12 as well, and its pathway may be similar to that of metformin.

First, BBR/DHB has a disruption of the Ca-dependent absorption at the terminal ileum and at TCII receptors synthesis.

At the outset, we consider that the hydrophobic tail of BBR/DHB, such as methyl group and phenyl group, may extend into the hydrocarbon core of membranes, which can influence the Ca-dependent absorption. Generally, the protonation sometimes occurs on ether bonds, BBR and DHB both have this functional group, so we think that BBR/DHB may give a positive charge to the surface of the membrane, which may alter membrane potentials, interfere with Ca-dependent membrane functions in the terminal ileum and reduce the VB12-IF levels. Furthermore, because of the hydrophobic tail and protonated ether bond of BBR/DHB, the synthesis of TCII receptors may also be interfered with, resulting in preventing combination with the proteolytic release of VB12 and reducing consequential VB12 level. In other words, BBR/DHB may act in general as a Ca channel blocker. Therefore, the levels of VB12-IF and VB12-TCII can be impacted by BBR/DHB because of a Ca-dependent ileal membrane antagonism, such that VB12 level may be affected.

Second, BBR/DHB exerts an alteration in intestinal balance such as short chain fatty acids content, gut microbiota diversity and richness.

BBR/DHB may have the similar pathway to delay glucose absorption, that altering small bowel motility and facilitating bacterial overgrowth. Moreover, BBR/DHB can produce the large number of short chain fatty acid (SCFAs)-producing bacteria, which may increase the proportion and content of SCFAs and then reduce the abundance and constituent ratio of intestinal microorganisms. Thus, BBR/DHB may induce the more significant gut microbial variations and then alter the ileal morphological structure compared with metformin. In addition, some patients, taken the BBR/DHB with the broad antibacterial properties, could have some incidental adverse symptoms of gastrointestinal discomfort and reduced bowel movements (constipation). See, e.g., also Zhang, X., et al., *Modulation of gut microbiota by berberine and metformin during the treatment of high-fat diet-induced obesity in rats*. Sci Rep, 2015. 5: p. 14405. A prior experiment in diabetic mice indicates that glucose metabolism was ameliorated by combined with BBR and stachyose (Sta, a prebiotic to enhance the growth and activity of beneficial bacteria), but both BBR alone and BBR with Sta reduced the gut microbial diversity and richness to the same extend attributing to the wide antibacterial characteristics of BBR. Li, C.-N., et al., Berberine combined with stachyose induces better glycometabolism than berberine alone through modulating gut microbiota andfecal metabolomics in diabetic mice. Phytotherapy Research, 2020. 34(5): p. 1166-1174.

Therefore, we consider and found that BBR/DHB with the broad antibacterial properties could decrease intestinal microbial activity significantly and subsequently transform the morphological structure of ileal, which may lead to VB12-IF level in decline and further VB12 reduction, competitive inhibition or inactivation of VB12 absorption.

In summary, there is an urgent need for finding an effective strategy for alleviating the above-described BBR/DHB related side effects including VB12 reduction. According to the present invention, it was particularly found that the BBR/DHB-related side effects (e.g., VB12 deficiency) could be successfully mitigated by combing with VB12. Specifically, the combination of BBR/DHB and vitamin B12 according to the present invention can particularly ameliorate vitamin B12 reduction by promoting transcobalamin II receptors synthesis, decreasing homocysteine levels and maintaining intestinal balance. Notably, it is believed that this invention is the first time to propose and conduct a combination of DHB and VB12.

The following examples are illustrative of select embodiments of the present invention and are not meant to limit the scope of the invention.

EXAMPLES

The high-fat diet (HFD, containing 60% fat by energy) mice at 8 weeks of age were divided into three groups: (1) non-supplement group (Con, n=5); (2) DHB supplement group (DHB, 100 mg/kg, n=5); (3) the combination of DHB and VB12 supplement group (DHB+VB12, DHB: VB12=100 mg/kg: 200 mg/kg, n=5). All mice were administered these things before each major meal for once daily (2 g/kg body weight) by gavage in normal saline solution for 3 months.

Example 1. Promoting TCH Receptors Synthesis and Decreasing Homocysteine Levels of HFD Mice Blood samples were collected from tail tips in a fasting state to measure serum VB12, serum homocysteine, glucose, and serum holo-transcobalamin II (holo-TCII, a biologically active fraction for TCII receptors synthesis) and weighed the mice for 0th, 2th, 4th, 6th, 8th, 10th and 12th week. After 3 months of supplementation, glycated hemoglobin (HbA1c) was measured. Also, the insulin tolerance test was performed after 3 months of supplementation after subcutaneous injection of insulin (0.4 U/kg, 0.05 ml/10 g body weight) for 0, 30, 90 minutes. Generally, biochemical VB12 and holo-TCII deficiency was defined as serum VB12<300 μg/mL and holo-TCII <50 μg/mL. Elevated homocysteine was defined as >15 M/L. Vitamin B12 levels and holo-TCII were measured by using immunoassay analyzer to confirm the improvement in TCII receptors synthesis and VB12 levels. Serum homocysteine levels were measured using the chemiluminescent microparticle immunoassay to show the VB12 levels. HbA1c was determined with automated glycohemoglobin analyzer, which can indicate the effect of blood glucose control during the trial. Glucose and insulin measurements were used by blood analyzer, which reflects the efficacy of glucose control at that time. Laboratory balances for weight to record the change of mice weight to exhibit the range of weight. FIG. 1 shows the results of blood glucose (FIG. 1a), serum VB12 (FIG. 1b), holo-TCII (FIG. 1c), insulin tolerance (Figure id), HbA1c (FIG. 1e) and serum homocysteine (Figure if) in HFD mice of the three groups.

Figure 1E:
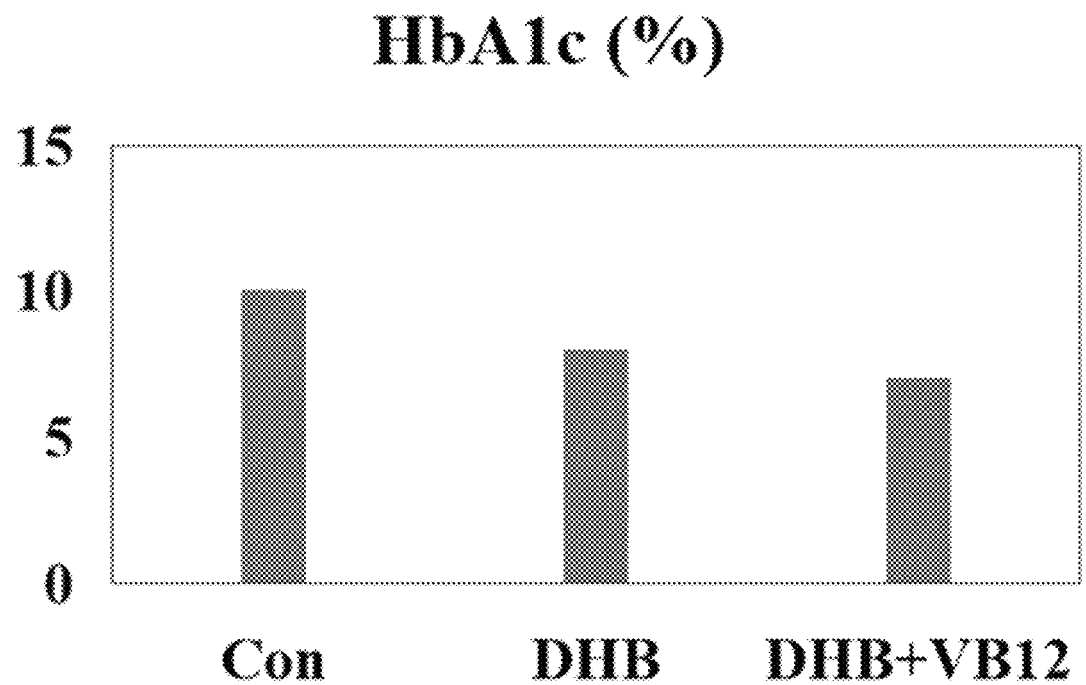
FIG. 1e is a graph of HbA1c of three groups of HFD mice (Con; DHB; DHB+VB12) without supplement, supplement with DHB, or with DHB+VB12 for 3 months, respectively.
Figure 1F:
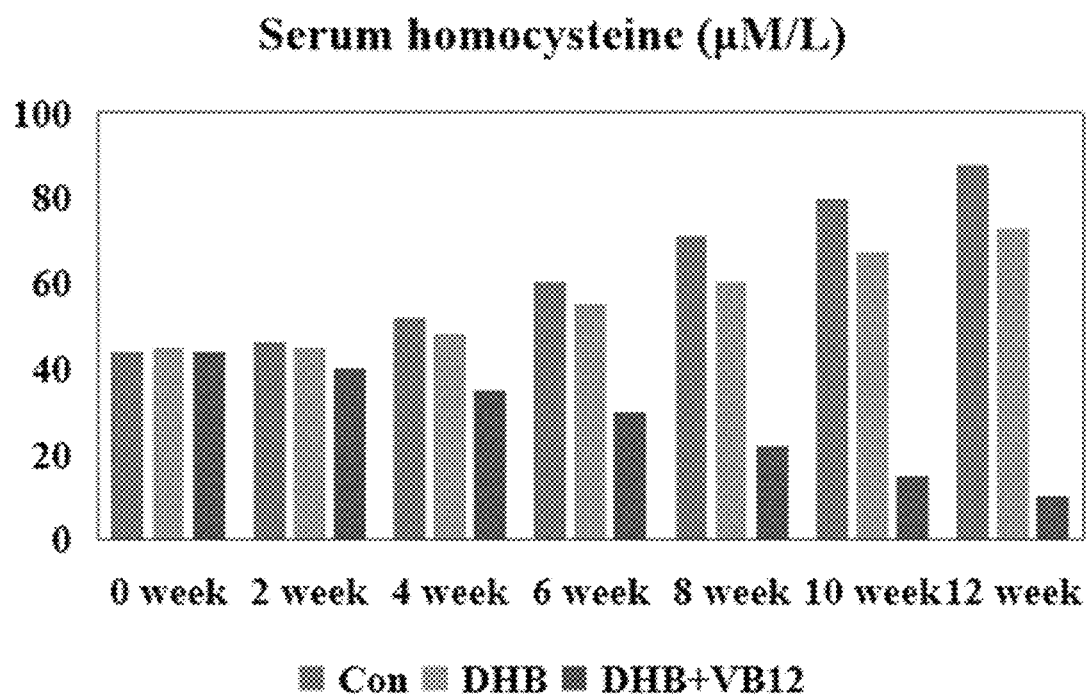
FIG. 1f is a graph of serum homocysteine levels of three groups of HFD mice (Con; DHB; DHB+VB12) at 0th, 2th, 4th, 6th, 8th, 10th and 12th weeks.

As shown in FIG. 1a, blood glucose levels were decreased significantly in the DHB and DHB+VB12 groups after supplementation. After three months, i.e., at 12th week, the blood glucose level was decreased by about 35% and even 47% in the DHB and DHB+VB12 groups, respectively, compared to the control group. After three months of supplementation, serum total VB12 (FIG. 1b) was significantly decreased in DHB group, but maintained basically the same at the normal level (>300 μg/mL) in DHB+VB12 group, as compared to other groups. After supplementation, serum holo-TCII (FIG. 1c) in DHB+VB12 group was increased significantly by about 93% compared to other groups. As shown in Figure id, after subcutaneous injection of insulin, blood glucose levels in all three groups were decreased over time, and at 90 minutes, blood glucose levels in the DHB and DHB+VB12 groups were about 15% and 31% lower than those in the control group, respectively, which shows DHB+VB12 could improve glycometabolism to a higher degree than DHB. As shown in FIG. 1e, after three months of supplementation, the HbA1c level was decreased by about 20% and even 30% in the DHB and DHB+VB12 groups, respectively, compared to the control group. Figure if shows homocysteine levels in DHB+VB12 group could be decreased significantly and even turned to normal levels (<15 IM/L). Therefore, DHB+VB12 supplement not only is good for blood glucose and insulin control, but also could promote TCII receptors synthesis and decrease homocysteine levels of HFD mice.

Example 2. Maintaining and improving intestinal balance such as SCFAs content, gut Microbiota Diversity and Richness of HFD Mice Stool samples were collected when mice were at 0th, 6th, and 12th week and stored in liquid nitrogen to test three major SCFAs contents including acetic acid, propionic acid, and butyric acid, in all groups by gas chromatography (GC). Total genomic bacterial DNA of the gut microbiome was also extracted from fecal samples using stool DNA kits to analyze the gut microbiota diversity and richness. The gut microbiome composition was analyzed based on 16S rRNA. The detailed process is as follows: Each raw 16S rRNA read was considered for the following criteria: (1) a perfect match to the barcode in at least one end; (2) a BLAST match to at least one end of the 16S rRNA gene V3-V4 region primers; (3) between 400 bp and 600 bp in length, excluding barcodes and primers; and (4) no more than two undetermined bases. Reads that did not meet these requirements were excluded from further analyses. High-quality reads were then aligned against the Greengenes database using the nearest alignment space termination algorithm to remove low-quality sequences, including potential chimeric sequences. A total of 160,223 operational taxonomic units (OTUs) were obtained at a similarity level of 97%. The most abundant sequence of each OTU among all the samples was selected as the representative sequence. OTU quantitative data were then used to calculate Shannon's diversity index and rarefaction estimate. Rarefaction and Shannon diversity index analyses indicated that the sequencing depth covered rare new phylotypes and most of the diversity. FIG. 2 indicates the results of acetic acid (FIG. 2a), propionic acid (FIG. 2b), butyric acid (FIG. 2c) contents, and the rarefaction (FIG. 2d) and Shannon diversity (FIG. 2e) estimates of the gut microbiome.

Figure 2A:
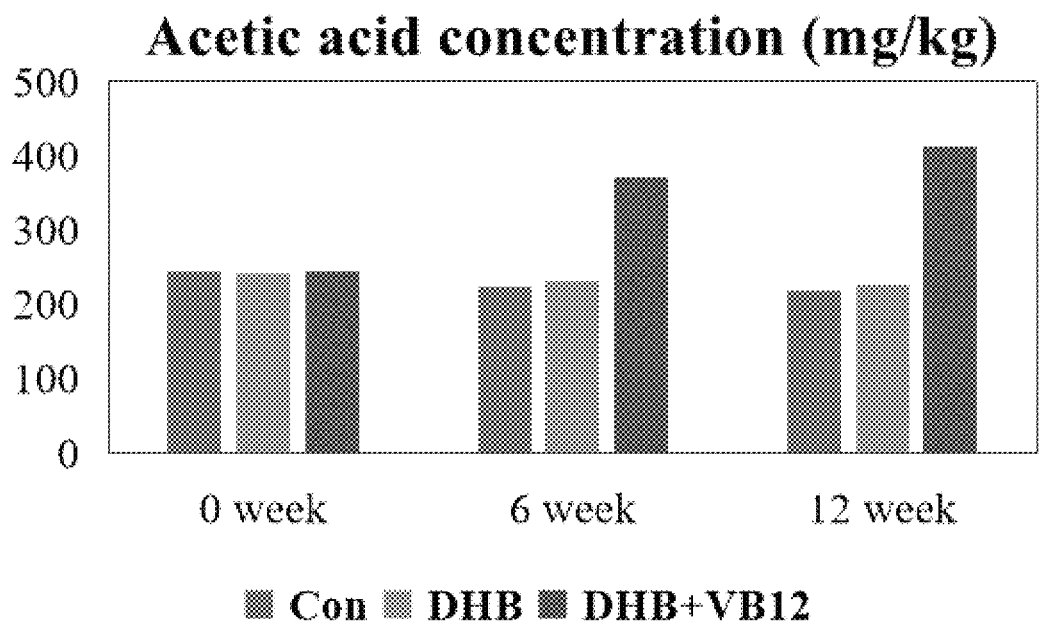
FIG. 2a is a graph of acetic acid contents in feces of three groups of HFD mice (Con; DHB; DHB+VB12) at 0th, 6th and 12th weeks.
Figure 2B:
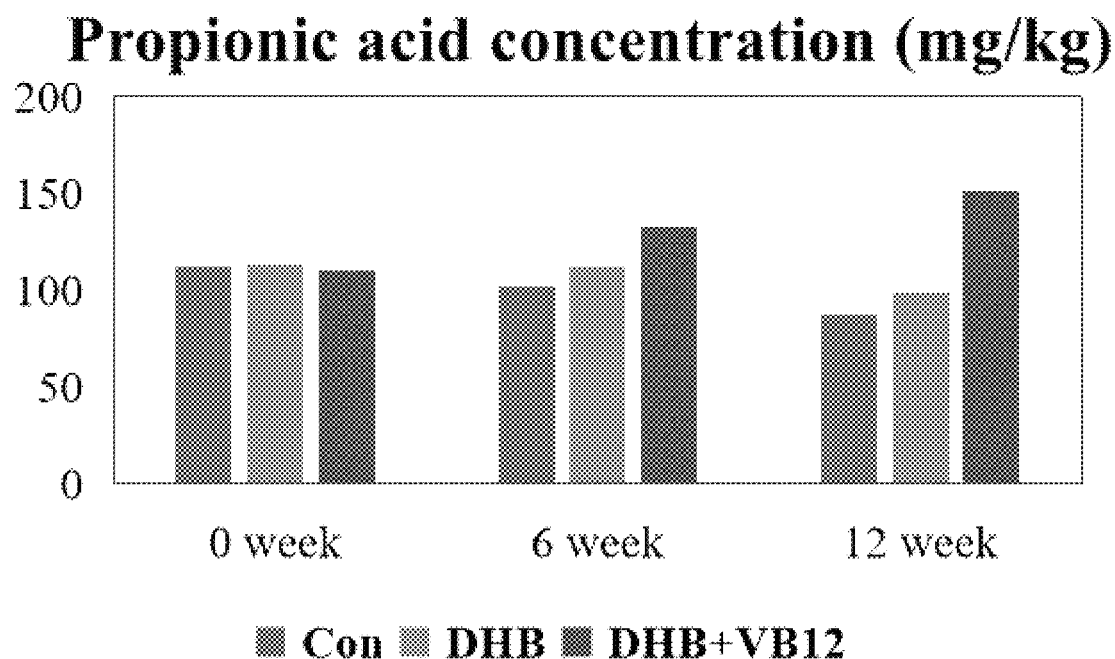
FIG. 2b is a graph of propionic acid contents in feces of three groups of HFD mice (Con; DHB; DHB+VB12) at 0th, 6th and 12th weeks.
Figure 2C:
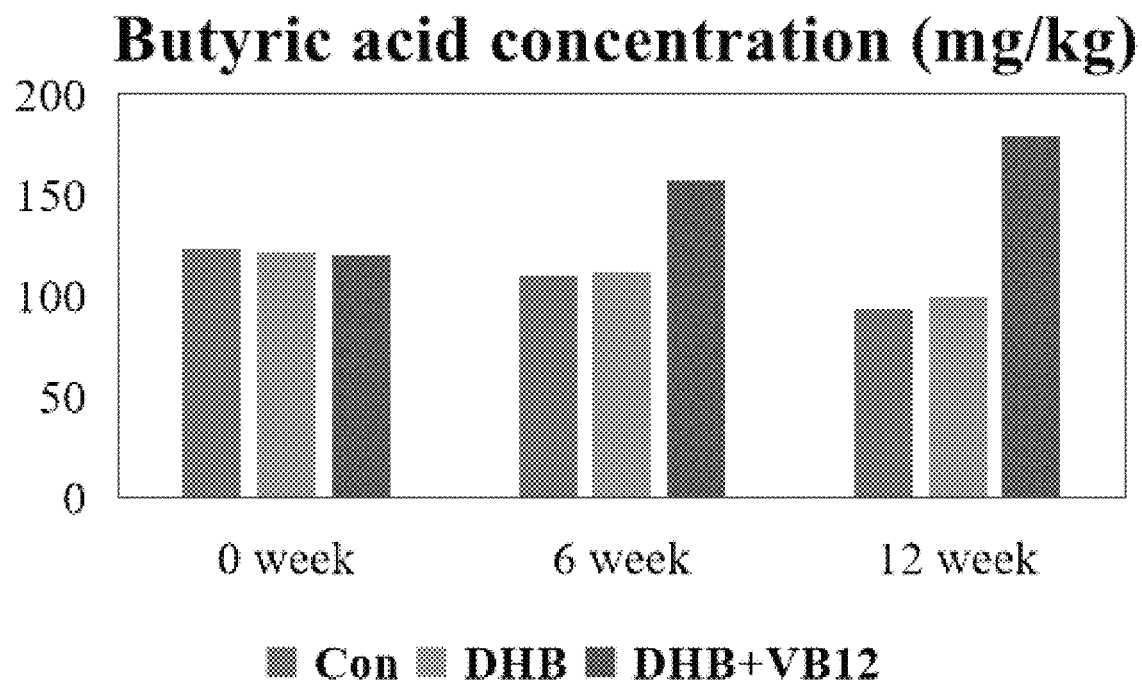
FIG. 2c is a graph of butyric acid contents in feces of three groups of HFD mice (Con; DHB; DHB+VB12) at 0th, 6th and 12th weeks.
Figure 2D:
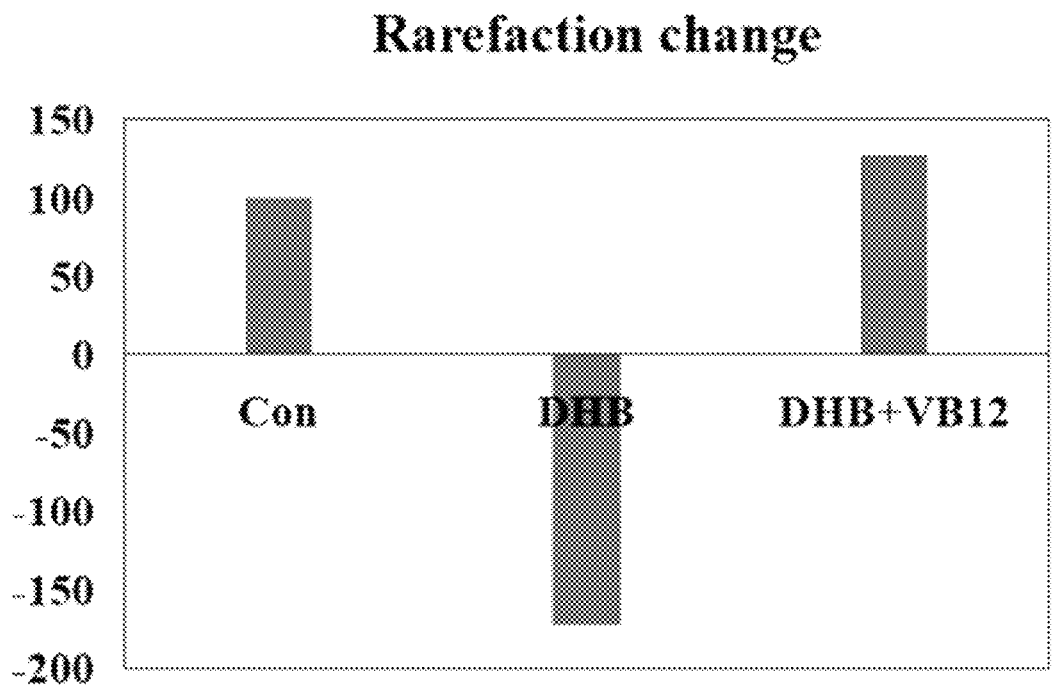
FIG. 2d is a graph of the rarefaction estimates of the gut microbiome of three groups of HFD mice (Con; DHB; DHB+VB12).
Figure 2E:
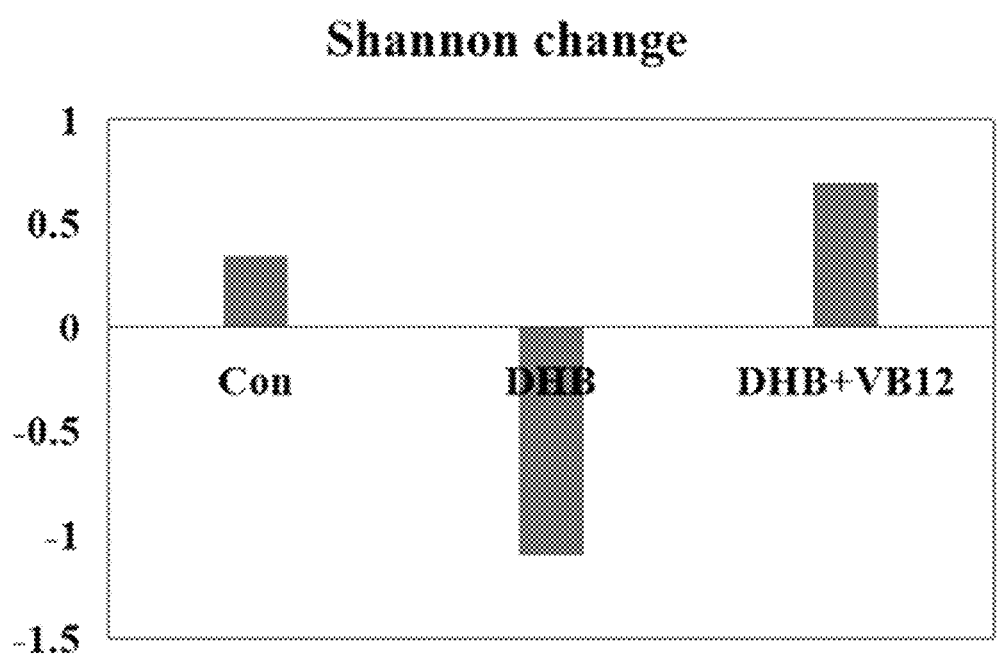
FIG. 2e is a graph of the Shannon diversity estimates of the gut microbiome of three groups of HFD mice (Con; DHB; DHB+VB12).

As shown in FIG. 2a-2c, levels of acetic acid, propionic acid, and butyric acid in the DHB+VB12 supplement group were significantly higher than in the non-supplement and DHB supplement groups. At 12th week, for the DHB+VB12 group, the content of acetic acid, propionic acid and butyric acid was 88%, 74% and 92% higher than that of the control group, and 82%, 53% and 79% higher than that of the DHB group, respectively. In other words, DHB+VB12 could improve and recover the SCFA content to a certain extent in HFD mice's feces. Moreover, DHB+VB12 could enhance the richness and diversity of the gut microbiome compared to other groups (FIG. 2d-2e). Overall, DHB+VB12 could maintain and improve intestinal balance such as SCFAs content, gut microbiota diversity and richness of HFD mice.

Although in the examples of the present application, DHB and VB12 were administered in a ratio of 1:2, this ratio may vary depending on various situations. The ratio of DHB and VB12 may include other ratios, such as 32:68 to 68:32, 16:84 to 84:16, 6:94 to 94:6 or even 2:98 to 98:2, etc.

Although specific embodiments and examples of this invention have been illustrated herein, it will be appreciated by those skilled in the art that any modifications and variations can be made without departing from the spirit of the invention. The examples and illustrations above are not intended to limit the scope of this invention. Any combination of embodiments of this invention, along with any obvious their extension or analogs, are within the scope of this invention. Further, it is intended that this invention encompass any arrangement, which is calculated to achieve that same purpose, and all such variations and modifications as fall within the scope of the appended claims.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

Other Embodiments

It is to be understood that while the invention has been described in conjunction with the detailed description thereof and accompanying figures, the foregoing description and accompanying figures are only intended to illustrate, and not limit the scope of the invention, which is defined by the scope of the appended claims. Other aspects, advantages, and modifications are within the scope of the following claims. All publications referenced herein are incorporated by reference in their entireties.

What is claimed is:

1. A method of maintaining or improving intestinal balance in a mammal, the method comprising
administrating to the mammal an effective amount of
(i) berberine (BBR), or a pharmaceutically acceptable salt, acid, or ester thereof, wherein the BBR is dihydroberberine (DHB) which is a hydrogenated derivative of BBR; and
(ii) vitamin B 12 (VB12) in a ratio of the DHB over the VB12 at 2:98 to 98:2 by weight,
to obtain intestinal balance of short chain fatty acid (SCFAs) contents or gut microbiota diversity and richness in the mammal.

2. The method of claim 1, wherein the BBR and the VB12 are prepared as a food, a drink, a supplement, or a pharmaceutical formulation.

3. The method of claim 1, wherein the BBR and the VB12 are in the form of suppository, tablet, pill, granule, powder, film, (micro)capsule, aerosol, tonic, liquid suspension, injection or syrup.

4. The method of claim 1, wherein the BBR and the VB12 are administered by one or multiple routes selected from the group consisting of oral, intravenous injectable, intramuscular injectable, intraperitoneal, and sublingual administrations.

5. The method of claim 1, wherein the BBR and the VB12 preserve Ca-dependent membrane function at the terminal ileum, promote cell surface transcobalamin II (TCII) receptors synthesis, and/or increase VB 12-IF (intrinsic factor) levels and decrease homocysteine levels of mammals daily.

6. The method of claim 1, wherein the BBR and VB12 are configured for administration at a dosage ranging from 20 mg to 600 mg per serving.

7. The method of claim 1, wherein the DHB is administered as a first component separately packaged from VB12, wherein the VB12 is administered as a second component.

8. The method of claim 1, wherein the DHB and VB12 are administered by:
(a) administering a first effective amount of the DHB at a first time point; and
(b) administering a second effective amount of VB12 at a second time point different than the first time point.

9. The method of claim 1, further comprising one or more of:
measuring serum level of VB12 of the mammal;
measuring serum level of holo-transcobalamin II (holo-TCII) of the mammal; and
measuring serum level of glycated hemoglobin (HbA1c) of the mammal.

10. The method of claim 1, wherein the method further controls blood glucose or body weight or treats diabetes.

* * * * *